United States Patent [19]

Miwa et al.

[11] 4,229,539

[45] Oct. 21, 1980

[54] β-GALACTOSIDASE AND PRODUCTION THEREOF

[75] Inventors: Tan Miwa; Reisuke Kobayashi, both of Shizuoka; Kiyoshi Takita, Shimizu, all of Japan

[73] Assignee: Kumiai Chemical Industry Co., Ltd., Tokyo, Japan

[21] Appl. No.: 6,575

[22] Filed: Jan. 26, 1979

[30] Foreign Application Priority Data

Feb. 6, 1978 [JP] Japan .................................. 53/12102

[51] Int. Cl.$^2$ .............................................. C12N 9/38
[52] U.S. Cl. ..................................... 435/207; 435/933
[58] Field of Search .................... 195/62, 65; 435/207

[56] References Cited

PUBLICATIONS

Derwent Publication 065394 of Japan Kokai 51-142593 Aug. 12, 1976.

*Primary Examiner*—Lionel M. Shapiro
*Attorney, Agent, or Firm*—Haight, Rosfeld, Noble & Santa Maria

[57] ABSTRACT

A new β-galactosidase is now provided which is highly effective to digest lactose and stable at acidic pH values and thermally stable. The β-galactosidase is produced by *Penicillium multicolor* in high yield and is isolated from the culture medium of this microorganism in an inexpensive and easy way.

7 Claims, No Drawings

β-GALACTOSIDASE AND PRODUCTION THEREOF

BACKGROUND OF THE INVENTION

This invention relates to a new β-galactosidase enzyme which in active form is used to digest or hydrolyze lactose into glucose and galactose. The new β-galactosidase is stable at acidic pH values predominating in the digestive organs of human beings and is stable at ambient and elevated temperatures on storage. This invention further relates to a fermentation process for the production of this new β-galactosidase by cultivating a microorganism of the genus *Penicillium* and particularly *Penicillium multicolor*.

β-Galactosidase is an enzyme which hydrolyzes the lactose present in the milk of mamalian animals to produce glucose and galactose. In recent years, this enzyme has called public attention as it is useful to improve or treat therapeutically the dyspeptic disorder of infants which are not capable of digesting lactose. The enzyme is also useful in the processing of various milk products.

Some kinds of β-galactosidase are already produced by commercial processes comprising cultivating a bacterium, yeast or fungus and isolating these β-galactosidases from the culture or culture broth of the microorganism. However, all of the known β-galactosidases are not satisfactory because they have one or more certain drawbacks with respect to their activity and stability as well as the yield of production.

Known β-galactosidases produced by microorganisms include the ones produced by bacteria such as lactic-acid bacteria and the ones produced by yeasts such as *Saccharomyces fragilis*. The known β-galactosidases produced by bacteria and yeasts are intercellular enzymes which remain within the cell body of the bacterium or yeast, therefore it is necessary to remove and extract these enzymes out of the cell body of these microorganisms. The preparation of these intercellular enzyme products needs a number of production stages, and besides, it is difficult to recover these intercellular enzyme products in high yield.

On the other hand, it is known that some β-galactosidases are produced as the extracellular enzyme by fungi of the genus Aspergillus such as *Aspergillus niger* (see Japanese patent publication No. 21078/74), *Aspergillus oryzae* (Japanese patent application pre-publication "Kokai" No. 151385/76), *Aspergillus awamori* (Japanese patent publication No. 22709/74), by fungi of the genus Macrophomina (Japanese patent application pre-publication "Kokai" No. 117677/76), by fungi of the genus Sclerotium (Japanese patent application pre-publication "Kokai" No. 116291/74) and by fungi of the genus Tricoderma (Japanese patent application pre-publication "Kokai" No. 62688/74).

Among these known β-galactosidases which are produced as the extracellular enzyme, the ones which are produced by *Aspergillus niger* and *Aspergillus awamori* as well as by the fungi of the genus Sclerotium are acidic β-galactosidase which show the optimum pH at a highly acidic value of 2 to 3.5 and hence are of limited applications.

Furthermore, the known β-galactosidases produced by *Aspergillus oryzae* and by fungi of the genus Macrophomina or the genus Tricoderma are differentiated from the new β-galactosidase which is produced by *Penicillium multicolor* according to this invention, with respect to their optimum temperature value, the optimum pH value, the temperature range and the pH range at which these enzymes are stable. All of the above-mentioned known fungi, except *Aspergillus oryzae* FERM-P 1680, have a very poor ability to produce the β-galactosidase as the extracellular enzyme.

*Aspergillus oryzae* FERM-P 1680 has a favorably high ability to produce β-galactosidase in a high potency, but the β-galactosidase produced by this particular strain can be inactivated at acidic pH value of 2.5 to 3.0 and hence shows a lower stability at the acidic pH values, as compared to the new β-galactosidase according to this invention. When the β-galactosidase of *Aspergillus oryzae* FERM-P 1680 is administered as a digestive drug to men, it is often useless as it is very likely to be inactivated at a pH value of 2.5 to 3.0 which are normally predominating in the cavity of the stomach.

In general, enzymatic preparations containing known β-galactosidase are of low stability upon storage. There are methods of stabilizing these enzymatic preparations by freezedrying (see Japanese patent publication No. 50390/72, for example) and methods of stabilizing these enzymatic preparations by incorporating inositol therein (see Japanese patent application pre-publication "Kokai" No. 9783/76) in order to prevent the degradation of the β-galactosidase.

Moreover, it is also known that *Penicillium frequentans* Westling (identified as FERM-P 3085) produces a β-galactosidase which is stable at a pH value of 3 to 5 at 4° C., the optimum pH being 3.5 to 4.5; *Penicillium luteum* Sopp (identified as FERM-P 3091) produces a β-galactosidase which is stable at a pH value of 3.5 to 8 at 4° C., the optimum pH being 4.0 to 5.0; *Penicillium citrinum* ATCC 9849 (identified as FERM-P 3086) produces a β-galactosidase which is stable at a pH value of 3.5 to 8 at 4° C., the optimum pH being 4.0 to 5.0; *Penicillium glaucum* Link (identified as FERM-P 3090) produces a β-galactosidase which is stable at a pH value of 3.5 to 8 at 4° C., the optimum pH being 4.0 to 5.0; *Penicillium chrysogenum* Thom IFD 4626 (identified as FERM-P 3088) produces a β-galactosidase which is stable at a pH value of 3 to 8 at 4° C., the optimum pH being 4.0 to 5.0; and *Penicillium notatum* Westling (identified as FERM-P 3087) produces a β-galactosidase which is stable at a pH value of 3.5 to 8 at 4° C., the optimum pH being 4.0 to 5.0. However, these Penicillium species can only produce the above-mentioned β-galactosidases in poor yield which is not commercially satisfactory. Additionally, the known β-galactosidases produced by these Penicillium species are not entirely satisfactory because they are not stable at pH values of 2.5 to 3.0 predominating in the stomach of human beings and because they can be inactivated completely by heating at an elevated temperature of about 65° C. for 15 minutes at pH 6.

SUMMARY OF THE INVENTION

The present invention deals with a new β-galactosidase which can be readily produced in high yield in a commercial scale and which is suitable for wide applications. It has been found that a known microorganism, *Penicillium multicolor* produces in a high yield new β-galactosidase which exhibits excellent enzymatic properties, in particular a useful high pH stability, and a useful high thermal stability. This new β-galactosidase can be obtained by cultivating the known strains of *Penicillium multicolor* in a culture medium, either liquid or solid, containing an assimilable carbon source and nitrogen source to produce and accumulate the enzyme in the medium, and then isolating the desired enzyme from the medium.

According to a first aspect of this invention, there is provided a powdery β-galactosidase isolated from the culture medium of *Penicillium multicolor* and having the following characteristics:

a. having a relative β-galactosidase activity of 224% for o-nitrophenyl-β-D-galactopyranoside and of 186% for p-nitrophenyl-β-D-galactopyranoside when assumed that the relative β-galactosidase activity is 100% for lactose;

b. having a molecular weight of about 120,000 when determined according to the gel-filtration method;

c. being active at pH of 2.5 to 7, the optimum pH being 4.5;

d. said β-galactosidase activity being lost by heating at pH 6 and at 75° C. for 15 minutes, the optimum temperature being at 55° C.;

e. said β-galactosidase activity being stable in a pH range of 2.5 to 8.0 when standing at 4° C. for 24 hours;

f. said β-galactosidase activity being kept stable at 100% at 60° C. and reduced to 60% at 65° C., to 25% at 70° C. and to 0% at 75° C. when standing at pH 6 for 15 minutes;

g. said β-galactosidase activity being inhibited by about 20% by the presence of mercuric ion ($Hg^{++}$) but being not substantially inhibited by the presence of ferrous ion ($Fe^{++}$) and cupric ion ($Cu^{++}$) at the metal ion concentration of $10^{-3}M$; and h. having an iso-electric point of 5.37 when measured according to an electrophoresis method.

The new β-galactosidase of this invention is stable at a pH value of 2.5 to 3.0 which is usually shown by the digestive juice produced by the stomach of men. Usually, the pH value predominating in the stomach cavity varies depending on the nature and quantity of foods taken in the stomach and the time lapsed from the intake of foods as well as according to the individual difference. The pH value in the stomach cavity normally shows a value of 4 to 5 after the intake of milk of cow and any milk products. Accordingly, it is very advantageous that the new β-galactosidase of this invention has the optimum pH of 4.5. In addition, the new β-galactosidase of this invention is advantageously characterized by its high stability at ambient temperature and at an elevated temperature of up to 60° C., so that it can be stored for a long period of time without affecting in any measure for stabilization. For instance, the new β-galactosidase of this invention is not substantially inactivated even when it was stored in the form of a powdery enzyme preparation in a sealed vessel at 45° C. for 1 month. The residual β-galactosidase activity remains at about 95% or more even when it was stored at 45° C. for 1 month in open air of a relative humidity of 50% to 70%. Therefore, the new enzyme of this invention has many advantages as compared to the known β-galactosidases which are of low stability and normally need to be stored in cold.

According to a second aspect of this invention, there is provided a process for the production of a β-galactosidase, which comprises:

a. cultivating a strain of *Penicillium multicolor* in a culture medium containing assimilable carbon and nitrogen sources to produce and accumulate the β-galactosidase in the medium, and b. then isolating the desired β-galactosidase from the medium.

DETAILED DESCRIPTION OF THE INVENTION

The microorganism, *Penicillium multicolor* used in this invention is a known species which is described in the "Japanese Federation of Culture Collections of Microorganisms" Catalogue, page 103, edited in 1968 by a Japanese depository "Institute for Fermentation (IFO)", Osaka, Japan. For the purpose of this invention, *Penicillium multicolor* KU-O-132 strain is suitable. This *Penicillium multicolor* KU-O-132 strain has been deposited in another Japanese depository "Fermentation Research Institute", Agency of Industrial Science & Technology of Japan, Inage, Chiba City, Japan as of 25th January, 1978 under depository number FERM-P 4375 and also has been deposited unrestrictedly in the American Type Culture Collection, U.S.A., under ATCC No.

Morphological properties common to the above-mentioned strains of *Penicillium multicolor* are briefly described below.

(1) Macroscopic observations (after incubation at 25° C. for 10 days on Czapek's agar medium):

Colonies of 30 to 40 mm in diameter are produced by the growth of *Penicillium multicolor*. The surface of the growth is radially wrinkled and covered with a dense and velvety layer composed of conidiums of deeply bluish green to greyish green color. The periphery of the growth shows orange to yellow color in width of 1 to 2 mm. The reverse of the growth shows yellow to brown color.

(2) Microscopic observations (after incubation at 25° C. for 10 days on Czapek's agar medium):

i. Penicillia: Monoverticillape ii. Conidiophore: Straight and vertical without branching, and 2-3 microns wide and broadened at the tips thereof.

iii. Sterigma: 8 to 14 sterigmas are grown in dense crowd.

iv. Conidium: Spherically or ovally shaped and 2 to 3 microns in diameter. The surface is smooth.

In carrying out the process of this invention, a strain of *Penicillium multicolor* may be cultivated either in a liquid culture medium or in a solid culture medium using known fermentation techniques, preferably under aerobic conditions. The culture medium used for fermentation may contain one or more of natural nutrients such as wheat bran, rice bran, defatted soybean meal and cotton seed meal as the basic components. The culture medium may contain also lactose, starch, glucose, arabinose and xylose as the carbon source and ammonium sulfate, sodium nitrate, peptone, malt extract and yeast extract as the nitrogen source, if necessary. Inorganic salts such as phosphates, magnesium salt and calcium salt may be incorporated in the culture medium, if desired. It is generally suitable to effect the cultivation of *Penicillium multicolor* at an incubation temperature of 10° to 35° C., preferably of 25° to 33° C. and in the environment having a pH value of 4 to 9, preferably of 5 to 7.5 for a period of 1 to 8 days, though the cultivation conditions may vary depending on the manner of cultivation employed. The production of the new β-galactosidase of this invention normally reaches a maximum in 2 to 6 days of incubation.

In a solid cultivation, the new β-galactosidase can be produced at a potency of about 1,000 units per gram of the solid culture medium. In a liquid cultivation, the new enzyme can be produced at a potency of about 150 units per 1 ml of the liquid culture medium. This high productivity of the new enzyme by *Penicillium multicolor* is about 10 to 30 times as much as the productivity of the known β-galactosidases by the known β-galactosidase-producing strains mentioned hereinbefore, except the *Aspergillus oryzae* FERM-P 1680.

In order to recover and isolate the new β-galactosidase of this invention from the culture medium of *Penicillium multicolor* where the enzyme has been produced and accumulated through the cultivation of this microorganism, the liquid culture medium or solid culture medium may be processed using known techniques for the recovery of enzymes, and the enzyme recovered may be purified in a known manner for the purification of enzymes. The liquid culture medium may be freed from the solid matter, for example, by filtration or centrifugation, and the broth filtrate so obtained is then concentrated by distillation under reduced pressure or by means of dialytic membrane and subsequently subjected to a salting-out process with ammonium sulfate or a precipitating process with acetone and/or ethanol to precipitate a crude powder of the new β-galactosidase. The solid culture medium may be extracted with water, and the resulting aqueous extract may be processed in the same way as the above-mentioned broth filtrate. The culture medium itself, the broth filtrate and the aqueous extract as such may be utilized as a crude β-galactosidase, if desired. For further purification of the crude β-galactosidase, it may be subjected to a conventional technique for purification of enzymes, such as ion-exchange method, gel-filtration method, dialysis, adsorption method and protein-precipitating method. When the concentrated broth filtrate or aqueous extract containing the new β-galactosidase dissolved therein is mixed with acetone to an acetone concentration of 30% to 40% by weight, substantially all of the β-galactosidase can be precipitated therefrom to give a β-galactosidase powder which, upon drying, shows a high β-galactosidase potency of about 34.8 units/mg. The process of this invention is therefore advantageous in that it makes possible the use of the inexpensive and commercially available acetone-precipitation method in order to recover a powdery β-galactosidase of a high potency. The powdery β-galactosidase of about 34.8 units/mg in potency usually does not need to be purified further as long as it is orally administered to the lactose-incompatible patients. As a digestive drug, it may either be formulated into an orally administrable powder, granules or tablets in admixture with a pharmaceutically acceptable carrier such as starch and sugar or may be dissolved in milk or any drinks to be taken by the patients.

The potency of the new β-galactosidase of this invention may be estimated according to a conventional assay method in the following manner:

One ml of a substrate solution containing 3.7 mg/ml of o-nitrophenyl-β-D-galactopyranoside in water, two ml of 0.2 M MacIlvanic buffered solution (pH 4.5) and one ml of the enzyme solution are mixed with each other, and the mixture is heated at 37° C. for 15 minutes to effect the enzymatic reaction. Subsequently, the reaction mixture is mixed with 4 ml of an aqueous solution of 1 M sodium carbonate to stop the reaction. The reaction mixture is subjected to a colorimetric analysis at a wave length of 420 mμ to determine the content of the o-nitrophenol produced, with reference to a standard curve for the colorimetric analysis of o-nitrophenol. When the enzyme can produce one μ mol of o-nitrophenol in one minute, this enzyme is estimated to have 1 unit in potency.

The new β-galactosidase of this invention is now compared in its enzymatic properties with the known β-galactosidase of *Penicillium citrinum* which is representative of the known β-galactosidases produced by the other Penicillium species described in the aforesaid Japanese patent application pre-publication "Kokai" No. 142593/76. The results of this comparison are briefly summarised in the following Table.

TABLE 1

| | Substrate Specifity Substrate (glycosides) | New enzyme of this invention | β-Galactosidase of P. citrinum |
|---|---|---|---|
| (1) | | Relative Activity(%) | |
| | Lactose | 100 | 100 |
| | o-Nitrophenyl-β-D-galactopyranoside | 224 | 398 |
| | p-Nitrophenyl-β-D-galactopyranoside | 186 | 288 |
| (2) | Molecular weight (estimated by a gel-filtration method) | ca. 1200,000 | ca. 100,000 |
| (3) | Optimum pH | 4.5 | 4–5 |
| (4) | Active pH (namely, the pH range where the enzyme is active) | 2.5–7 | 3.5–8 |
| (5) | Optimum Temperature | 55° C. | 50° C. |
| (6) | Active Temperature (namely, the temperature range where the enzyme is active) | Less than 75° C. | Less than 60° C. |
| (7) | pH Stability (namely, the pH range where the enzyme is stable for 24 hours) | 2.5–8.0 | 3.5–8.0 |
| (8) | Thermal Stability, namely, the residual β-galactosidase activity estimated after standing at pH 6 for 15 minutes and at: | | |
| | 60° C. | 100% | 50% |
| | 65° C. | 60% | 0% |
| | 70° C. | 25% | 0% |
| | 75° C. | 0% | 0% |
| (9) | Effect of metal ions (at $10^{-3}$ molar concentration) | | |
| | Ferrous ($Fe^{++}$) | Substantially not inhibited | Substantially not inhibited |
| | Cupric ($Cu^{++}$) | Substantially not inhibited | Substantially inhibited |
| | Mercuric ($Hg^{++}$) | Inhibited by about 20% | Substantially not inhibited? |
| (10) | Iso-electric point (determined by electrophoresis) | 5.37 | 6.41 |
| (11) | Solubility in aqueous organic solvents | | |
| | Water containing 40% by weight of methanol | 0% | 87% |
| | Water containing 50% by weight of methanol | 0% | 71% |
| | Water containing 40% by weight of ethanol | 0% | 82% |
| | Water containing 50% by weight of ethanol | 0% | 64% |
| | Water containing 40% by weight of acetone | 0% | 91% |
| | Water containing 50% by weight of acetone | 0% | 72% |

The invention is now illustrated with reference to the following Examples.

EXAMPLE 1

A solid culture medium comprising a mixture of 10 g of wheat bran, 10 g of defatted soybean meal and 20 ml of water was placed in a 500 ml conical flask and sterilized by heating at 120° C. for 15 minutes in an autoclave, and the sterilized culture medium was then inoculated with a slant culture of *Penicillium multicolor* KU-O-132 (identified as FERM-P 4375). The inoculated medium was incubated in a sterile air at 28° C. for 4 days, and the incubated medium was then admixed with 200 ml of water to extract β-galactosidase into the aqueous phase. The mixture was filtered to remove the solid matter. The filtrate, that is, the aqueous extract showed a β-galactosidase potency of 228 units/ml.

EXAMPLE 2

A liquid culture medium (100 ml) containing 3% rice bran, 1% cotton seed meal, 0.25% mono-potassium phosphate and 0.15% di-potassium phosphate (pH 6.2) was placed in a 500 ml flask and then sterilized by heating in an autoclave. The sterilized culture medium was inoculated with a slant culture of *Penicillium multicolor* KU-O-132, and the inoculated medium was shake-cultivated at 28° C. for 3 days by being placed on a reciprocally shaking table. The incubated culture broth was filtered and the broth filtrate was found to show a β-galactosidase potency of 140 units/ml.

EXAMPLE 3

(a) A solid culture medium consisting of a uniform mixture of 1.5 kg of defatted soybean meal, 1.5 kg of cotton seed meal and 3 liters of water was placed as a layer in a large vat and then sterilized by heating in an autoclave. The sterilized culture medium was then inoculated with 150 g of a seed culture of *Penicillium multicolor* KU-O-132 which was prepared by incubating the aforesaid slant culture of this microorganism in a bran medium (a mixture of wheat bran and water at a ratio of 1:1 by weight) at 28° C. for 3 days. The inoculated medium was then statically incubated at 28° C. for 5 days, and the incubated medium (5.4 kg) was disintegrated and packed in a cylindrical column of glass through which water was subsequently passed by introducing the water at the top of the column. The extract solution (18 l) containing the desired enzyme was obtained as the effluent from the bottom of the column and was centrifuged to be freed from a small amount of the solid matter which was suspended in said extract solution. The resulting supernatant solution showed a β-galactosidase potency of 347 units/ml.

(b) This supernatant solution was concentrated to a volume of 4 liters by ultrafiltration and then to the concentrated solution was dropwise added 2.7 liters of acetone at a low temperature. The precipitate formed was removed by filtration and dried under reduced pressure to give 165 g of a powder of β-galactosidase of this invention which showed a high β-galactosidase potency of 34,800 units/g.

Recovery yield: 92%.

(c) The powder of β-galactosidase (potency: 34,800 units/g) obtained as above was further purified in the following way: β-galactosidase powder was dissolved in 0.01 M buffered acetate solution at pH 4.5 and the resulting solution was passed through a column of CM-cellulose to adsorb the enzyme in the column. The CM-cellulose column was then eluted gradiently with aqueous solutions of sodium chloride. The active fractions of the eluate were combined together and dialyzed with 0.01 M buffered phosphate solution at pH 7.0, and the enzyme solution so dialyzed was then passed through a column of DEAE-cellulose to effect the adsorption of the enzyme. This DEAE-cellulose column was subsequently eluted gradiently with aqueous solutions of sodium chloride. The active fractions of the eluate were combined together and then passed through a column of a gel-filtration agent ("SEPHADEX" G 150, a product of Pharmacia Co. Ltd., Sweden). The effluent passing out of the Sephadex column was collected in fractions, and such active fractions which showed the β-galactosidase potency at a constant level were combined together and concentrated under reduced pressure.

To the concentrated solution so obtained was dropwise added ethanol at a low temperature to precipitate the desired enzyme. The enzyme was removed by filtration and dried under reduced pressure to give a colorless and electrophoretically pure powder of the β-galactosidase which exhibited a potency of 170,000 units/g.

Recovery yield: 50%.

What we claim is:

1. A powdery β-galactosidase isolated from the culture medium of *Penicillium multicolor* and having the following characteristics:
   a. having a relative β-galactosidase activity of 224% for o-nitrophenyl-β-D-galactopyranoside and of 186% for p-nitrophenyl-β-D-galactopyranoside when assumed that the relative β-galactosidase activity is 100% for lactose;
   b. having a molecular weight of about 120,000 as determined according to the gel-filtration method;
   c. being active at pH of 2.5 to 7, the optimum pH being at 4.5;
   d. said β-galactosidase activity being lost by heating at pH 6 and at 75° C. for 15 minutes, the optimum temperature being at 55° C.;
   e. said β-galactosidase activity being stable in a pH range of 2.5 to 8.0 when standing at 4° C. for 24 hours;
   f. said β-galactosidase activity being stable at 100% at 60° C. and reduced to 60% at 65° C., to 25% at 70° C. and to 0% at 75° C. when standing at pH 6 for 15 minutes;
   g. said β-galactosidase activity being inhibited by about 20% by the presence of mercuric ion ($Hg^{++}$) but being not substantially inhibited by the presence of ferrous ion ($Fe^{++}$) and cupric ion ($Cu^{++}$) at a metal ion concentration of $10^{-3}M$; and
   h. having an iso-electric point of 5.37 when measured according to an electrophoresis method.

2. A β-galactosidase according to claim 1, obtained from *Penicillium multicolor* KU-O-132 identified as FERM-P 4375.

3. A β-galactosidase according to claim 1, in the form of a powder having a relative β-galactosidase activity of about 34,800 units/g.

4. A process for the production of a β-galactosidase, which comprises:
   a. cultivating a strain of *Penicillium multicolor* in a culture medium containing assimilable carbon and nitrogen sources to produce and accumulate the β-galactosidase in the medium, and
   b. then isolating the β-galactosidase from the medium.

5. A process according to claim 4 in which liquid cultivation of *Penicillium multicolor* is conducted at a temperature of 10°–40° C. and at a pH of 4–9 for a period of 1 to 8 days under aerobic conditions.

6. A process according to claim 4 which comprises:
a. cultivating *Penicillium multicolor* in a culture medium containing bran as assimilable nitrogen source to produce and accumulate the β-galactosidase in the medium,
b. extracting the medium with water to give an aqueous extract solution of the enzyme,
c. precipitating the enzyme from the extract by addition of acetone; and
d. drying the resulting precipitate.

7. A process according to claim 4 which comprises:
a. cultivating *Penicillium multicolor* in a liquid culture medium containing assimilable nitrogen and carbon sources under aerobic conditions to produce and accumulate the enzyme in the liquid medium,
b. filtrating the liquid culture broth to remove solid matter,
c. concentrating the clear filtrate obtained,
d. precipitating the enzyme from the concentrated filtrate by the addition of acetone, and
e. drying the resulting precipitate.

* * * * *